United States Patent
Koehler et al.

(10) Patent No.: US 9,761,021 B2
(45) Date of Patent: Sep. 12, 2017

(54) DARK FIELD COMPUTED TOMOGRAPHY IMAGING

(71) Applicant: KONINKLIJKE PHILIPS N.V., Eindhoven (NL)

(72) Inventors: Thomas Koehler, Norderstedt (DE); Bernhard Johannes Brendel, Norderstedt (DE); Ewald Roessl, Henstedt-Ulzburg (DE); Udo van Stevendaal, Ahrensburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 271 days.

(21) Appl. No.: 14/397,878

(22) PCT Filed: May 13, 2013

(86) PCT No.: PCT/IB2013/053881
§ 371 (c)(1),
(2) Date: Oct. 30, 2014

(87) PCT Pub. No.: WO2013/171657
PCT Pub. Date: Nov. 21, 2013

(65) Prior Publication Data
US 2015/0124927 A1    May 7, 2015

Related U.S. Application Data

(60) Provisional application No. 61/646,520, filed on May 14, 2012.

(51) Int. Cl.
G06T 11/00    (2006.01)
G01T 1/29    (2006.01)
(Continued)

(52) U.S. Cl.
CPC .............. G06T 11/005 (2013.01); A61B 6/48 (2013.01); G01N 23/201 (2013.01);
(Continued)

(58) Field of Classification Search
CPC .... A61B 6/00; A61B 6/02; A61B 6/03; A61B 6/40; A61B 6/4035; A61B 6/4064;
(Continued)

(56) References Cited

U.S. PATENT DOCUMENTS

2010/0310037 A1* 12/2010 Wang .................... A61B 6/032
378/6
2011/0293064 A1    12/2011 Huang et al.
2013/0094625 A1    4/2013 Huang et al.

FOREIGN PATENT DOCUMENTS

WO    2012000694 A1    1/2012

OTHER PUBLICATIONS

Wang, Ge, et al. "Varying Collimation for Dark-Field Extraction", (2009) Hindawi Publishing Corp., International Journal of Biomedical Imaging. vol. 2009, Article ID 847537, pp. 1-7.*
(Continued)

Primary Examiner — Anastasia Midkiff

(57) ABSTRACT

A method includes obtaining a dark-field signal generated from a dark-field CT scan of an object, wherein the dark-field CT scan is at least a 360 degree scan. The method further includes weighting the dark-field signal. The method further includes performing a cone beam reconstruction of the weighted dark-field signal over the 360 degree scan, thereby generating volumetric image data. For an axial cone-beam CT scan, in one non-limiting instance, the cone-beam reconstruction is a full scan FDK cone beam reconstruction. For a helical cone-beam CT scan, in one non-limiting instance, the dark-field signal is rebinned to wedge geometry and the cone-beam reconstruction is a full scan
(Continued)

aperture weighted wedge reconstruction. For a helical cone-beam CT scan, in another non-limiting instance, the dark-field signal is rebinned to wedge geometry and the cone-beam reconstruction is a full scan angular weighted wedge reconstruction.

23 Claims, 7 Drawing Sheets

(51) Int. Cl.
G01N 23/20 (2006.01)
G01N 23/201 (2006.01)
A61B 6/00 (2006.01)
G01N 21/88 (2006.01)
G01N 23/04 (2006.01)

(52) U.S. Cl.
CPC ..... *G01N 23/20083* (2013.01); *G01T 1/2907* (2013.01); *G06T 11/006* (2013.01); *A61B 6/42* (2013.01); *G01N 23/046* (2013.01); *G01N 2021/8822* (2013.01); *G01N 2021/8825* (2013.01); *G01N 2223/054* (2013.01); *G06T 2207/10081* (2013.01)

(58) Field of Classification Search
CPC ....... A61B 6/4078; A61B 6/4085; A61B 6/42; A61B 6/4291; A61B 6/44; A61B 6/48; A61B 2576/00; H05G 1/00; H05G 1/64; G01T 1/00; G01T 1/16; G01T 1/1606; G01T 1/161; G01T 1/29; G01T 1/2907; G01T 1/2914; G01N 23/00; G01N 23/046; G01N 23/20; G01N 23/20008; G01N 23/20083; G01N 23/201; G01N 2021/88; G01N 2021/8806; G01N 2021/8822; G01N 2021/8825; G01N 2223/00; G01N 2223/045; G01N 2223/05; G01N 2223/054; G01N 2223/10; G01N 2223/101; G01N 2223/1016; G01N 2223/40; G06T 11/005; G06T 11/006
See application file for complete search history.

(56) References Cited

OTHER PUBLICATIONS

Chen, Guang-Hong, et al. "Small-angle Scattering Computed Tomography (SAS-CT) using a Talbot-Lau Interferometer and a Rotating Anode X-ray Tube: Theory and Experiments", (Jun. 7, 2010) Optical Society of America, Opt. Express, vol. 18, No. 12, pp. 1-15.*

Cong, w., et al. "X-ray Dark-field Imaging Modeling", (May 18, 2012) Optical Society of America, J. Opt. Soc. Am. A, vol. 29, No. 6, pp. 908-912.*

Bech, M., et al.; Quantitative x-ray dark-field computed tomography; 2010; Phys. Med. Biol.; 5529-5539.

Blevins, N., et al.; X-ray dark-field computed tomography using a grating interferometer setup; 2010; Proc. SPIE Medical Imaging; 7622:76220P.

Chen, G-H., et al.; Small-angle scattering computed tomography (SAS-CT) using a Talbot-Lau interferometer and a rotating anode x-ray tube: theory and experiments; 2010; Opt. Express; 18(12)12960-12970.

Cong, W., et al.; Dark-field Tomography: Modeling and Reconstruction; 2010; arXiv.org 14 pages http://arXiv.org/abs/1003.2155v1.

Pfeiffer, F., et al.; Hard-X-ray dark-field imaging using a grating interferometer; 2008; Nature Materials; 7:134-137.

Shechter, G., et al.; High-resolution images of cone beam collimated CT scans; 2005; IEEE Trans. on Nuclear Science; 52(1)247-255.

Wang, Z., et al.; New solution for reconstruction problem about grating-based dark field computed tomography; 2009; Proc. Fully 3D Image Reconstruction in Radiology and Nuclear Science; 438-441.

* cited by examiner

DARK FIELD COMPUTED TOMOGRAPHY IMAGING

CROSS REFERENCE TO RELATED APPLICATIONS

This application is a national filing of PCT application Serial No. PCT/IB2013/053881 filed May 13, 2013, published as WO 2013/171657 A1 on Nov. 21, 2013, which claims the benefit of U.S. provisional application Ser. No. 61/646,520 filed May 14, 2012, which is incorporated herein by reference.

The following generally relates to dark field CT imaging and more particularly to reconstructing dark field CT image data.

In conventional CT imaging, contrast is obtained through the differences in the absorption cross-section of the constituents of the scanned object. This yields good results where highly absorbing structures such as bones are embedded in a matrix of relatively weakly absorbing material, for example the surrounding tissue of the human body. However, in cases where different forms of tissue with similar absorption cross-sections are under investigation (e.g., mammography or angiography), the X-ray absorption contrast is relatively poor. Consequently, differentiating pathologic from non-pathologic tissue in an absorption radiograph obtained with a current hospital-based X-ray system remains practically impossible for certain tissue compositions.

Dark-field (or grating-based differential phase-contrast) imaging overcomes the above-noted contrast limitation. Generally, dark-field imaging utilizes X-ray gratings, which allow the acquisition of X-ray images in phase contrast, which provides additional information about the scanned object. With dark-field imaging, an image is generated that is based on the scatter components of the X-ray radiation diffracted by the scanned object. Very slight density differences in the scanned object then can be shown at very high resolution. Dark-field imaging is discussed in greater detail in Pfeiffer et al., "Hard X-ray dark-field imaging using a grating interferometer," Nature Materials 7, pp 134-137.

Wang et al., "New solution for reconstruction problem about grating-based dark field computed tomography, Proc. Fully 3D 2009, 438, and Bech et al., "Quantitative x-ray dark-field computed tomography," Phys. Med. Biol. 55(2010) 5529 argue that the dark field image is a line integral of a physical quality, namely the second-moment of the small scattering distribution. Both Wang et al. and Bech et al. propose using a simple conventional filtered back-projection for reconstructing dark-field images. However, these publications are based on experiments using parallel beams and/or relatively small field of views (non-full body) and do not take into account the position of the object with respect the gratings.

Unfortunately, simple conventional filtered back-projection (FBP) is not well-suited for fan beam geometries and larger fields of view such as those used to scan humans in hospitals for diagnostic purposes since it implicitly assumes a data acquisition model that deviates from the true acquisition as will be discussed in more detail later. This mismatch of the true acquisition and the simplified model used in standard FBP leads to artifacts (like capping or cupping). Thus, there is an unresolved need for other approaches for reconstructing dark-field image data.

Aspects described herein address the above-referenced problems and others.

In one aspect, a method includes obtaining a dark-field signal generated from a dark-field CT scan of an object, wherein the dark-field CT scan is at least a 360 degree scan. The method further includes weighting the dark-field signal. The method further includes performing a cone beam reconstruction on the weighted dark-field signal over the 360 degree scan, thereby generating volumetric image data.

In another aspect, an imaging system includes a focal spot that emits radiation that traverses an examination region, an interferometer that filters the emitted radiation for a dark-field imaging scan of an object, a detector array that detects radiation traversing the examination region, and a reconstructor that reconstructs the dark-field signal over 360 degrees, generating volumetric image data.

In another aspect, a computer readable storage medium is encoded with computer readable instructions, which, when executed by a processor, cause the processor to: obtain a dark-field signal generated from at least a 360 degree dark-field CT scan of an object, weight the dark-field signal, and perform a cone beam reconstruction on the weighted dark-field signal over 360 degrees, thereby generating volumetric image data.

The invention may take form in various components and arrangements of components, and in various steps and arrangements of steps. The drawings are only for purposes of illustrating the preferred embodiments and are not to be construed as limiting the invention.

FIGS. 1-3 schematically illustrates attenuation and magnification for attenuation contrast imaging.

FIGS. 4-6 schematically illustrates attenuation and magnification for dark field imaging.

FIGS. 7 and 8 schematically illustrate an example imaging system with an interferometer for dark-field imaging.

FIG. 9 schematically illustrates attenuation for a ray complementary to the ray of FIG. 6.

Figure 12:
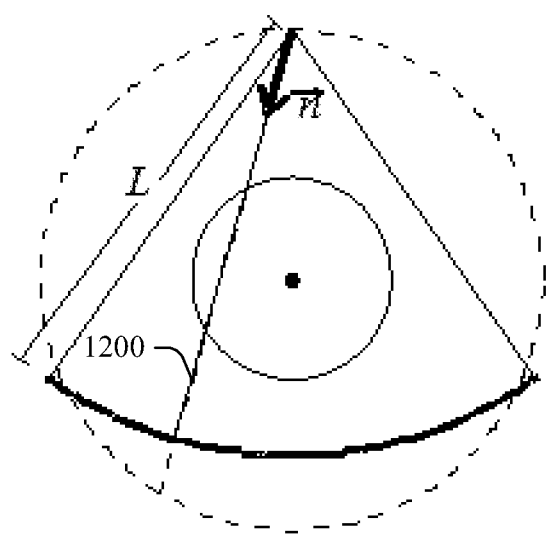
Figure 13:
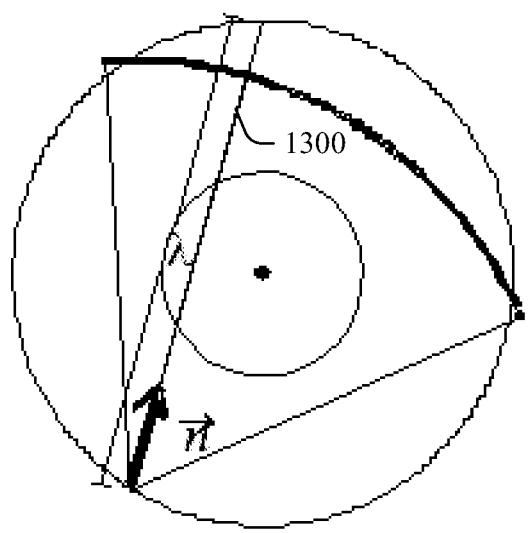

FIGS. 12 and 13 respectively show another depiction of complementary rays over a full (or 360 degree) scan.

Figure 14:
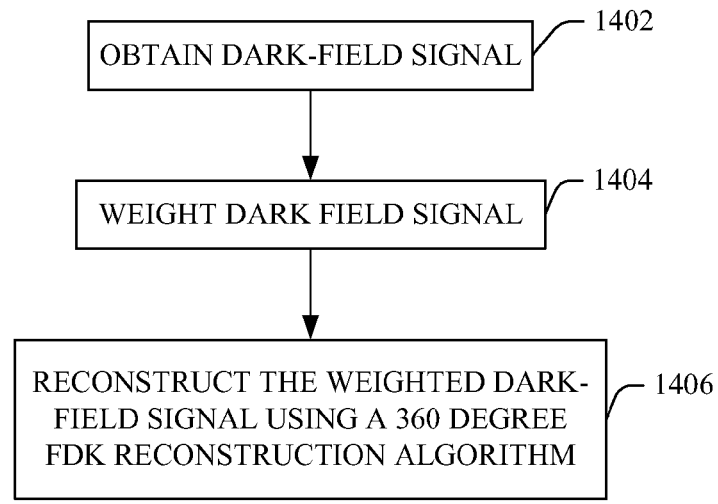

FIG. 14 illustrates an example axial cone-beam CT dark field reconstruction method.

Figure 15:
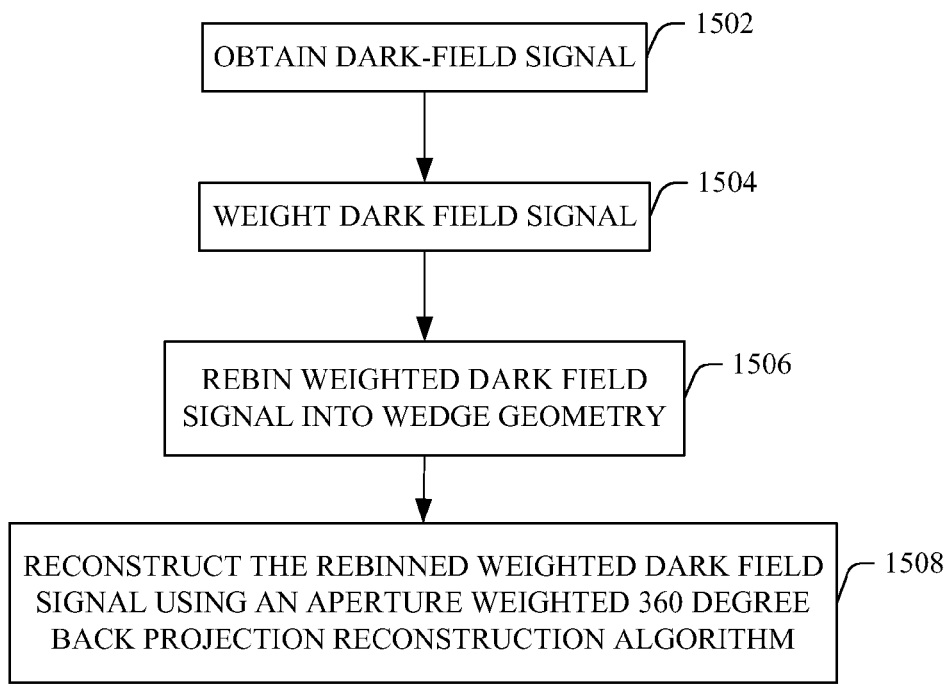

FIG. 15 illustrates an example helical cone-beam CT dark field reconstruction method.

Conventional dark-field imaging reconstruction algorithms do not take into account "inverse signal magnification." Generally, "inverse signal magnification" is a magnification that scales the height of the detected signal inversely with respect to the position of an object between the source of radiation and the detector. That is, the height of the detector signal for an object closer to the radiation source will be smaller (FIG. 4, 402) than the height of the detector signal for the object positioned farther from the source (FIG. 5, 500).

"Inverse signal magnification" does not affect attenuation contrast imaging (FIGS. 1 and 2, 110 and 200), but it introduces artifact (e.g., blurring) into dark-field images, which may make it difficult to discriminate between tissue having similar contrast characteristics. The following describes an approach(s) for taking the "inverse signal magnification" into account with dark-field imaging by including a magnification term in the reconstruction algorithm or a reconstruction formulation which cancels the magnification from the reconstruction, thus, mitigating the artifacts introduced into dark field images thereby.

Turning to FIGS. 1-6, conventional filtered back-projection is not well-suited for dark-field signal reconstruction with larger fields of view such as those used to scan humans. This is discussed is greater detail next in connection with FIGS. 1-6.

Figure 1:
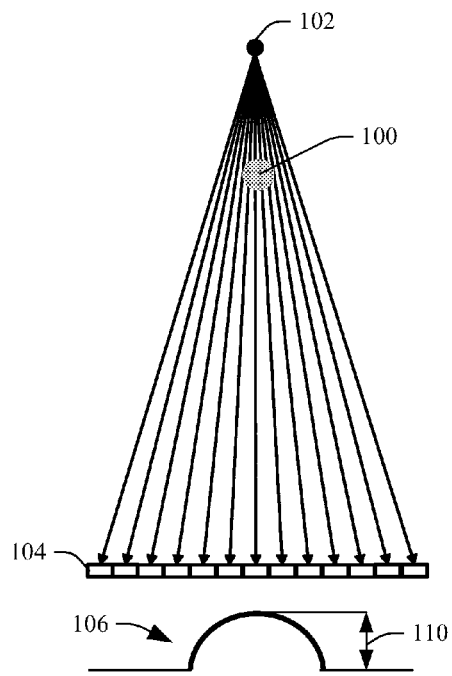
Figure 2:
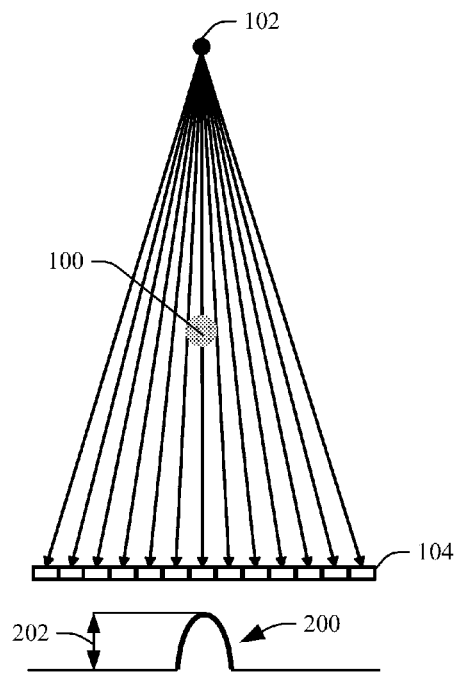

With attenuation contrast imaging, as shown in FIGS. 1-2, depending on a position of an object 100 between a source 102 and a detector array 104, the respective measured projections 106 and 200 are stretched and shortened depending on "size magnification" and signal heights 110 and 202 (i.e. values of line integrals) are the same.

Figure 3:
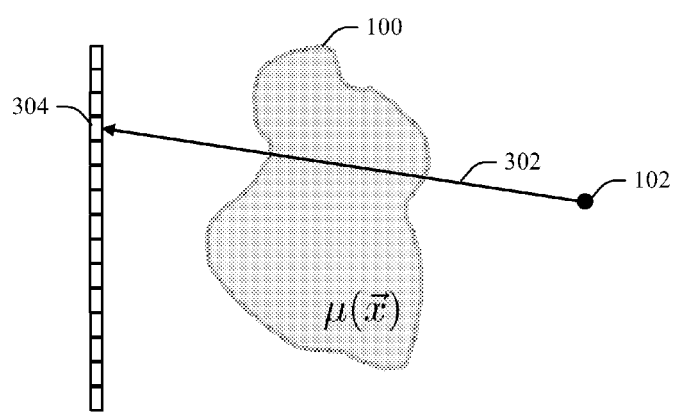

With attenuation contrast imaging, as shown in FIG. 3, an x-ray traverses along a path 302 from the source 102, through the object 100, to a detector pixel 304 of the detector array 104. The attenuation of the x-ray along the path 302 occurs exponentially, as shown in EQUATION 1:

$$I = I_0 e^{-\int_0^L \mu(\vec{s} + l\vec{n})dl} \quad \text{EQUATION 1:}$$

where I is the intensity at the detector pixel, $I_0$ is the unattenuated intensity, e is the base of the natural logarithm, L is the length of the x-ray from the source 102 through the object 100 to the detector pixel 306, $\mu$ is the attenuation coefficient, $\vec{s}$ is the source position, l is the length of the x-ray at a given unit vector $\vec{n}$ along the x-ray from 0 to L. Logging both sides of the equations renders a linear equation representing the line integral of the attenuation coefficient along the path 302, as shown in EQUATION 2:

$$m = -\ln\left(\frac{I}{I_0}\right) = \int_0^L \mu(\vec{s} + l\vec{n})dl \quad \text{EQUATION 2}$$

The "size magnification" is taken into account in conventional fan-beam FBP algorithms.

Figure 4:
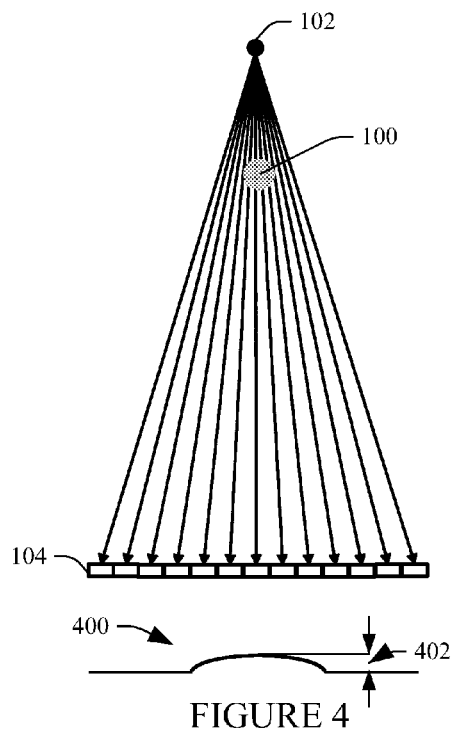
Figure 5:
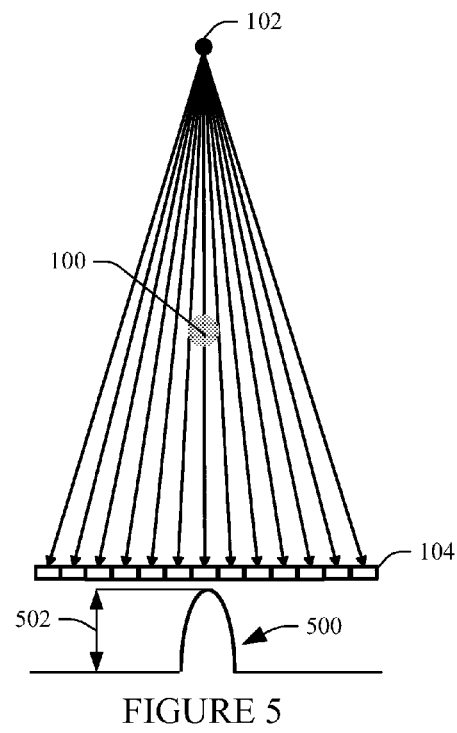

With dark field imaging, as shown in FIGS. 4 and 5, depending on the position of the object 100 between the source 102 and the detector array 104, the respective measured projections 400 and 500 are stretched and shortened depending on "size magnification," similar to attenuation contrast imaging, but signal heights 402 and 502 (i.e. values of line integrals) scale inversely with "inverse signal magnification."

Figure 6:
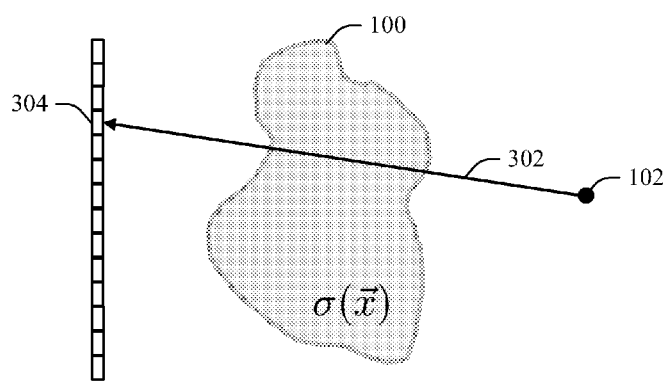

As shown in FIG. 6, for dark field imaging, the loss of visibility of the x-ray along the path 302 is as shown in EQUATION 3:

$$V = V_0 e^{-\int_0^L \frac{l}{L}\sigma(\vec{s}+l\vec{n})dl} \quad \text{EQUATION 3}$$

where V is the loss of visibility and $V_0$ is the initial visibility. The material property $\sigma$ that generates signal in this detection channel is denoted the diffusion coefficient. Logging both sides of the equations does not render the line integral of the diffusion coefficient along the path 302 in analogy to the attenuation coefficient but rather to a weighted line integral as shown in EQUATION 4:

$$m = -\ln\left(\frac{V}{V_0}\right) = \int_0^L \frac{l}{L}\sigma(\vec{s}+l\vec{n})dl. \quad \text{EQUATION 4}$$

The aim of dark field computed tomography is to reconstruct the spatial distribution of the diffusion coefficient $\sigma$ from a set of measurements of the dark field signal m. As used herein, this is referred to as "reconstructing the diffusion coefficient".

Similar to attenuation contrast imaging, the "size magnification" is taken into account in conventional fan-beam FBP algorithms; however, the "inverse signal magnification" (1/L) is not taken into account in conventional fan-beam FBP algorithms. The additional weighting l/L does not permit to use a conventional filtered back-projection to reconstruct the distribution of the diffusion coefficient. If the weighting factor barely changes over the object's extend, for example if the object is very small compared to the distance L, the additional weighting can be approximated to be constant or dropped.

Figure 7:
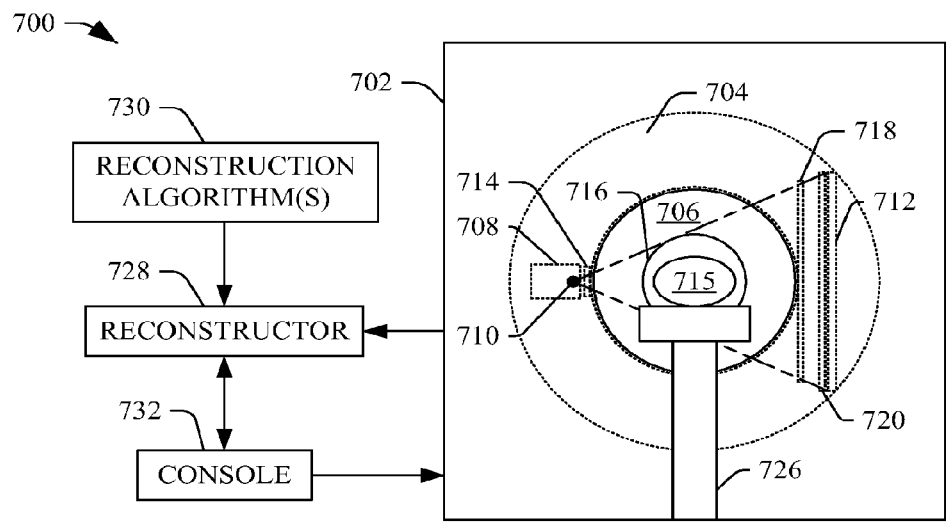

Turning to FIG. 7, an imaging system 700 such as a CT scanner is schematically illustrated. The CT scanner can be a full body, head, or small bore scanner. The imaging system 700 includes a generally stationary gantry 702, which houses a rotating gantry 704 that is rotatably supported by the stationary gantry 702 and rotates around an examination region 706 about a z-axis. The examination region includes a field of view 716 configured for scanning a human body 715 and/or an object.

A radiation source 708 (e.g., an X-ray tube) with a focal spot 710 is rotatably supported by the rotating gantry 704, rotates with the rotating gantry 704, and emits radiation. A radiation sensitive detector array 712 is located opposite the radiation source 708 across the examination region 706. The radiation sensitive detector array 712 detects radiation traversing the examination region 706 and generates a signal indicative thereof.

The imaging system 700 includes an X-ray imaging interferometer having three grating structures, a source grating 714, a phase grating 718 and an analyzer grating 720. The source grating 714, phase grating 718 and analyzer grating 720 respectively have grating periods and are separated by distances 722 and 724 that satisfy the Talbot conditions, which are discussed in detail in Pfeiffer et al., "Hard X-ray dark-field imaging using a grating interferometer," Nature Materials 7, pp 134-137.

The source grating 714 is adjacent to the focal spot 710 in the path of the radiation. The source grating 714 creates a beam of individually coherent, but mutually incoherent sources, which traverse an object 715 in the examination region 706. Generally, the radiation source 708 emits a polychromatic incoherent radiation beam, and the source grating, for example, an absorbing mask with transmitting slits, filters the emitted radiation beam, creating the individually coherent sources, which have sufficient spatial coherence for dark field imaging.

The phase grating 718 is located adjacent to the object 715 and receives the refracted coherent x-rays, which result in changes of the locally transmitted intensity through the phase grating 718. The analyzer grating 720 is adjacent to the detector array 712 in the path of the beam. Image formation using the gratings 718 and 720 is based on the principal that a phase object placed in an X-ray beam path causes slight refraction of the beam transmitted through the object, and imaging depends on locally detecting these angular deviations. The angle can be determined based on the arrangement formed by the gratings 718 and 720.

The gratings 718 and 720 can be considered a multi-collimator translating the angular deviations into changes of the locally transmitted intensity, which can be detected with a standard imaging detector. For weakly absorbing objects, the detected intensity is a direct measure of the object's local phase gradient. Higher precision of the measurement can be achieved by splitting a single exposure into a set of images taken for different positions of the grating 720. This also allows the separation of the dark field signal from other contributions, such as a non-negligible absorption of the object, or an already inhomogeneous wavefront phase profile before the object.

Figure 8:
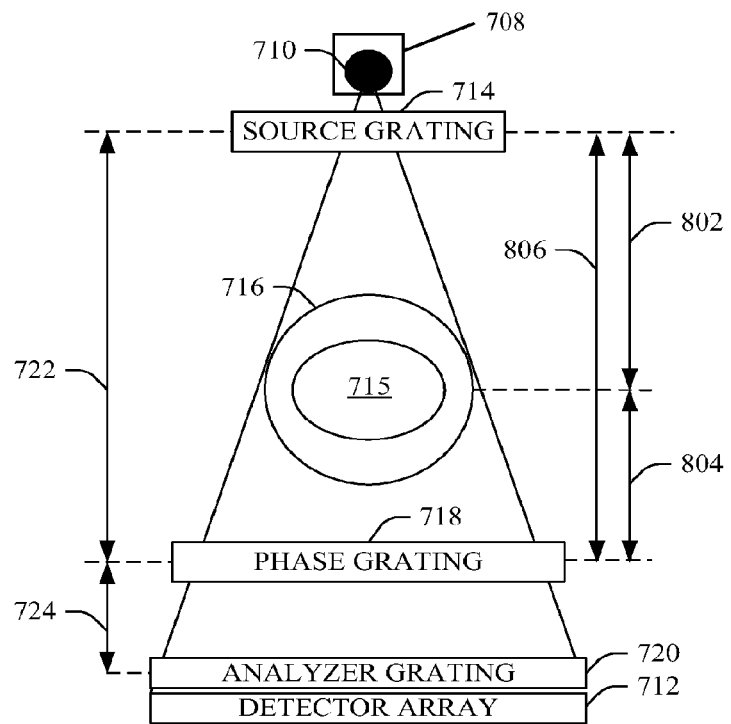

Generally, the object 715 causes slight refraction of coherent x-rays that is proportional to the local gradient of the real part of the refractive index of the object 715, and the angular deviation results in changes of the locally transmitted intensity through the phase grating 718 and the analyzer grating 720 that are detected by the detector array 110. FIG. 8 shows a more detailed view of the source grating 714, phase grating 718 and analyzer grating 720 in connection with the focal spot 710, the object 715 and the detector array 712.

A reconstructor 728 reconstructs the signal based on a reconstruction algorithm(s) 730, generating volumetric image data. As described in greater detail below, in one non-limiting instance, the reconstructor 728 utilizes a reconstruction algorithm that takes into account magnification of the object 715, which can be determined based on the location of the object 715 between the focal spot 710 and the phase grating 718.

The magnification can be estimated based on EQUATION 5:

$$M = (SO + OG)/SO, \quad \text{EQUATION 5:}$$

where SO represents a source grating-to-object distance 802, OG represents an object-to-phase grating distance 804, and SO+OG represents a source grating-to-phase grating (SG) distance 806. The magnification of a typical full body scanner is in a range of approximately 0.5 to 2.0. Note that although FIG. 8 shows a single point (the middle) of the object 112 where SO and OG are determined, for reconstruction, the SO and OG can be based on the relative position of a voxel being reconstructed with respect to other voxels, and the SO and OG for two different voxel may be different.

From EQUATION 5, the magnification increases with an increasing OG/decreasing SO. Unfortunately, the magnification of the object, if not taken into consideration, results in artifacts in the reconstructed diffusion coefficient, which degrades image quality. As described in detail bellow, taking the magnification into account mitigates such artifacts and improves contrast, which allows for better discrimination between tissue (e.g., tumor and tissue) with similar contrast. For example, taking the magnification into account mitigates blurring, resulting from the magnification, which may make it difficult to discriminate between tissue having similar contrast characteristics.

A subject support 726, such as a couch, supports the object 715 in the examination region 706. A general-purpose computing system or computer serves as an operator console 732. The console 732 includes a human readable output device such as a monitor and an input device such as a keyboard, mouse, etc. Software resident on the console 732 allows the operator to interact with and/or operate the scanner 700 via a graphical user interface (GUI) or otherwise.

As discussed above, the reconstructor 728 can employ a reconstruction algorithm that takes magnification of the object 715 into account. An example reconstruction algorithm is an algebraic reconstruction technique (ART) reconstruction algorithm, which is an iterative reconstruction algorithm. For a conventional attenuation contrast CT reconstruction, a suitable ART is shown in EQUATION 6:

$$x_j^{(n+1)} = x_j^{(n)} + \frac{b_i - \sum_k a_{ik} x_k^{(n)}}{\|a_i\|^2} a_{ij} \quad \text{EQUATION 6}$$

where $x_j^{(n+1)}$ is the jth voxel of the (n+1)th image, $x_j^{(n)}$ is the jth voxel of the previous image, $b_i$ is one the measured data (i.e., one particular line integral through the object), $a_{ik}$ is the contribution of the kth image voxel to the ith measured line integral, $a_i$ is the sum of all $a_{ik}$ over k. In this imaging model the elements $a_{ik}$ of the so-called system matrix A contain the contribution of a voxel k to a measured line integral i as the line intersection length of the geometrical ray with the voxel. If other basis function than voxels are used, e.g., blobs, then the line integral along the ray through the basis function is used.

To take into account magnification, the system matrix A is modified to include the magnification term M of EQUATION 6, rendering EQUATION 7:

$$x_j^{(n+1)} = x_j^n + \frac{b_i - \sum_k d_{ik} x_k^{(n)}}{\|d_i\|^2} d_{ij} \quad \text{EQUATION 7}$$

where $d_{ij}$ is an element of the dark field system matrix D with $d_{ij} = a_{ij}/M_{ij}$, where $M_{ij}$ is the geometrical magnification of the j-th image voxel when being projected onto the i-th detector pixel.

Figure 9:
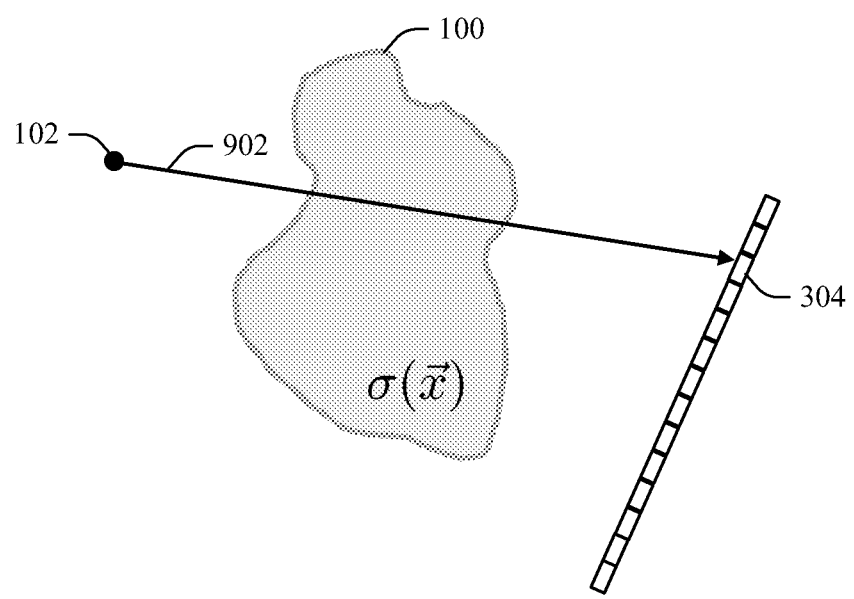

The following describes another suitable reconstruction. In FIG. 9, a complementary x-ray (the x-ray of FIG. 3 turned by 180 degrees) traverses along the path 902. The visibility V' is as shown in EQUATION 8:

$$V' = V_0' e^{-\int_0^{L'} \frac{l}{L'} \sigma(\vec{s}' - l\vec{n}') dl}, \quad \text{EQUATION 8}$$

where the primes indicate that the geometrical values relate to the complementary x-ray. Logging both sides of the equations renders the weighted line integral of the diffusion coefficient along the complementary path 902, as shown in EQUATION 9:

$$m' = -\ln\left(\frac{V'}{V_0'}\right) \quad \text{EQUATION 9}$$
$$= \int_0^{L'} \frac{l}{L'} \sigma(\vec{s}' + l\vec{n}') dl$$
$$= \int_0^{L} \frac{l}{L} \sigma(\vec{s}' - l\vec{n}') dl.$$

In Equation 9, the fact that by definition of the complementary ray, the relation $\vec{n}' = -\vec{n}$ holds true is exploited. Furthermore, it is assumed, for the sake of simplicity, L=L'. The source position for the complementary x-ray is somewhere on the ray of FIG. 3: $\vec{s}'' = \vec{s} + \lambda \vec{n}$ for some λ. Substituting this into EQUATION 9 renders EQUATION 10:

$$m' = \frac{1}{L} \int_0^L l\sigma(\vec{s} + (\lambda - l)\vec{n}) dl. \quad \text{EQUATION 10}$$

Changing the variables l'=λ-l renders EQUATION 11:

$$m' = \frac{1}{L}\int_{\lambda-L}^{\lambda}(\lambda-l')\sigma(\vec{s}+l'\vec{n})dl. \quad \text{EQUATION 11}$$

Assuming the diffusion coefficient distribution outside of the field of view is zero and substituting l=l', EQUATION 11 becomes EQUATION 12:

$$m' = \frac{1}{L}\int_{0}^{L}(\lambda-l)\sigma(\vec{s}+l\vec{n})dl. \quad \text{EQUATION 12}$$

Summing m and m' renders EQUATION 13:

$$m+m' = \frac{\lambda}{L}\int_{0}^{L}\sigma(\vec{s}+l\vec{n})dl. \quad \text{EQUATION 13}$$

For an axial 2D full scan, a weighted average for the ray 300 and the complementary ray can be computed as shown in EQUATION 14:

$$\frac{L}{\lambda}(m+m') = \int_{0}^{L}\sigma(\vec{s}+l\vec{n})dl, \quad \text{EQUATION 14}$$

which can be solved using a conventional filtered back projection to reconstruct the diffusion coefficient distribution.

EQUATION 14 requires acquisition of the complementary ray and, thus, EQUATION 14 cannot be used for cone-beam reconstruction. The following describes an approach that extends EQUATION 14 for cone beam reconstruction. FIGS. 12 and 13 respectively show another depiction of complementary rays 1200 and 1300 over a full (or 360 degree) scan.

Again, EQUATION 14 represents an average of the direct measurement m (e.g., ray 1200) and the complementary measurement m' (e.g., ray 1300) and is applied to the entire 360 degree acquisition, with the resulting sinogram reconstructed using a conventional filtered back projection reconstruction algorithm. In EQUATION 14, λ represents the cosine of the fan angle.

EQUATION 14 can be re-written, symbolically, by denoting the full original 360 degree sinogram data as D(α,φ), where α represents an angular position of the source 710 (FIG. 7) and φ represents a fan angle of a measured sample, and the sinogram of the complementary data as C(α,φ). The relationship between complementary data and direct data is C(α,φ)=D(α+π-2φ,-φ). Weighted complementary and weighted direct data are respectively represented as D'(α,φ) =(1/cos(φ))D(α,φ) and C'(α,φ)=(1/cos(φ))C(α,φ).

From this, the original, exact FBP reconstruction can be written as shown in EQUATION 15:

$$\sigma = \text{FBP}_F(D'(\alpha,\phi) + C'(\alpha,\phi)), \quad \text{EQUATION 15:}$$

where σ represents the linear diffusion coefficient, and F indicates fan-bean. The fan-beam sinograms can be rebinned to parallel beam geometry. EQUATION 15 can be re-written as shown in EQUATION 16:

$$\sigma = \text{FBP}_P(D'(r,\beta) + C'(r,\beta)), \quad \text{EQUATION 16:}$$

where P indicates parallel-beam, r represents a distance of a ray to the origin and β represents an angle with respect to the x-axis, and r≥0 and 0≤β<2π. As with EQUATION 14, EQUATIONS 15 and 16 require complementary data.

Leveraging the linearity of FBP, EQUATION 16 can be expressed as shown in EQUATION 17:

$$\sigma = \text{FBP}_P(D'(r,\beta)) + \text{FBP}_P(C'(r,\beta)). \quad \text{EQUATION 17:}$$

Since the complementary ray 1300 is also a direct ray (just 180 degrees or π apart from the direct ray 1200), EQUATION 17 can be expressed as EQUATION 18:

$$\sigma = \text{FBP}_P(D'(r,\beta)) + \text{FBP}_P(D'(r,\beta+\pi)). \quad \text{EQUATION 18:}$$

With EQUATION 18, the averaging that was done originally in projection domain is now postponed and performed in image domain after back-projection.

In EQUATION 18, the two FBP terms should be identical since both FBP terms operate on the entire 360 degree sinogram data with just the data being reshuffled with respect to the projection angles (with ramp-filtering and interpolation performed on the same data). As such, EQUATION 17 can be written as EQUATIONS 19 and 20, using D'(r,β) as an approximation for C'(r,β):

$$\sigma = \text{FBP}_P(D'(r,\beta)) + \text{FBP}_P(D'(r,\beta)), \text{ and} \quad \text{EQUATION 19:}$$

$$\sigma = 2\text{FBP}_P(D'(r,\beta)). \quad \text{EQUATION 20:}$$

Rebinning the parallel-beam data back into the original fan-beam geometry renders EQUATION 21:

$$\sigma = 2\text{FBP}_F(D'(\alpha,\phi)). \quad \text{EQUATION 21:}$$

EQUATIONS 20 and 21 allow for an extension to cone-beam geometry since no explicit averaging of the direct and complimentary rays is required. For example, for a 360 degree axial cone-beam CT scan, the conventional full scan FDK cone beam reconstruction can be applied to the weighted sinogram D'. An example FDK reconstruction is discussed in Feldkamp et al., "Practical cone-beam algorithm", J. Opt. Soc. Am. A/Vol. 1, No. 6/June 1984. Feldkamp et al. describes the general concept, including weighting with cone-angle and 3D BP with conventional weighting.

For a helical cone-beam CT scan, an aperture weighted wedge reconstruction can be applied to the weighted sinogram D', with a normalization over 2PI-partners. An example approach for a high-resolution aperture weighted wedge reconstruction is discussed in Shechter et al., "High-Resolution Images of Cone Beam Collimated CT Scans", IEEE Transactions on Nuclear Science 52(1), 247 (2005). In Shechter et al., a wedge-rebinning (the cone-beam extension of 2D parallel rebinning) is followed by a full scan back-projection with a weighting function. An angular weighted wedge (or extended wedge) reconstruction can be used with an angular weighting function that ensures that the weights of all views with distance 2π add to ½ independently.

FIGS. 10, 11, 14 and 15 illustrate example methods. It is to be appreciated that the ordering of the acts of these methods is not limiting. As such, other orderings are contemplated herein. In addition, one or more acts may be omitted and/or one or more additional acts may be included.

Figure 10:
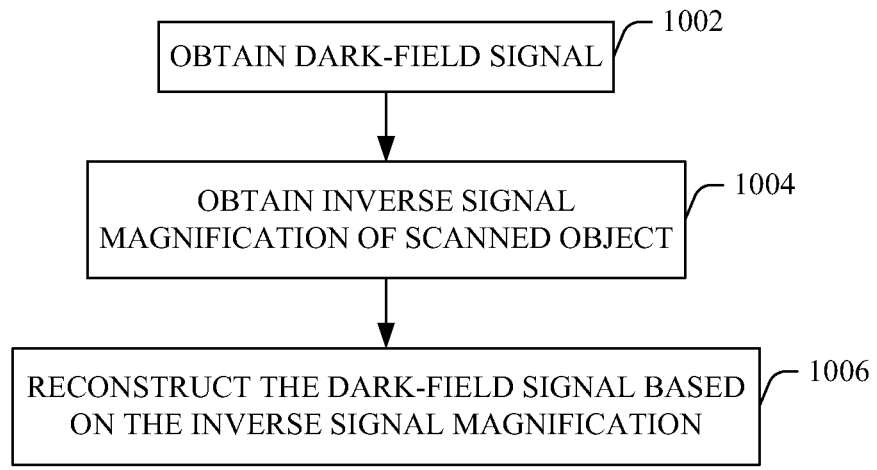
FIG. 10 illustrates an example method for reconstructing a dark field signal with a reconstruction algorithm that includes an inverse signal magnification of the scanned object.

FIG. 10 illustrates an example method.

At 1002, a dark-field signal is obtained for a scanned object.

At 1004, an inverse signal magnification of the scanned object is obtained.

At 1006, the dark-field signal is reconstructed using a reconstruction algorithm that includes the obtained magnification.

Figure 11:
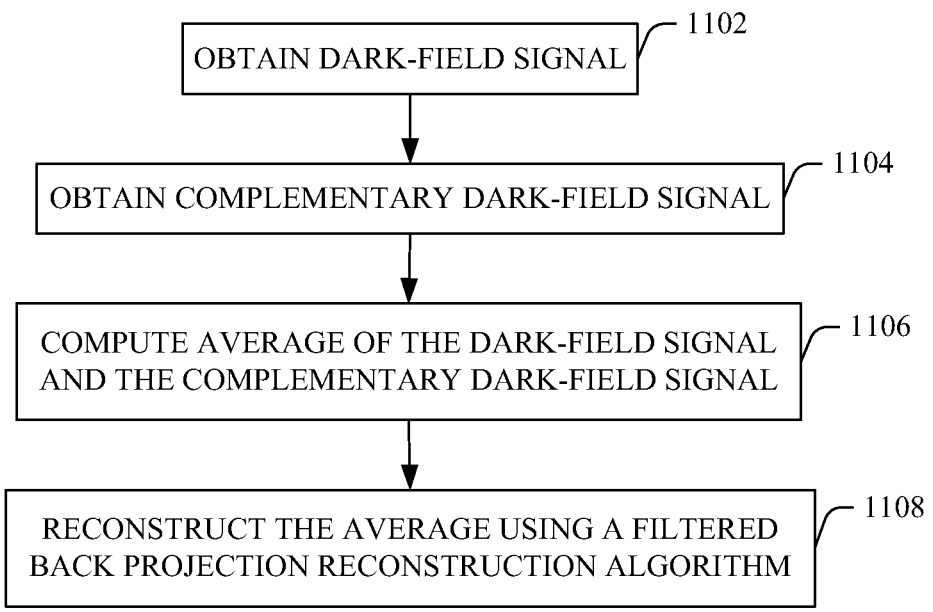
FIG. 11 illustrates an example method for reconstructing an average dark field signal with a filtered back projection reconstruction algorithm.

FIG. 11 illustrates another example method.

At 1102, a dark-field signal is obtained for a scanned object.

At 1104, a complementary dark-field signal is obtained for the scanned object. The signal and the complementary signal are 180 degrees apart.

At 1106, an average is computed based on the signal and the complementary signal.

At 1108, the average is reconstructed using a conventional filtered back-projection reconstruction algorithm.

FIG. 14 illustrates an example axial cone-beam CT dark field reconstruction method.

At 1402, a dark-field signal is obtained for a scanned object from a 360 degree scan.

At 1404, the dark field signal is weighted.

At 1406, a full scan FDK reconstruction algorithm is applied to the weighted dark field signal over the 360 degree scan, as described herein.

FIG. 15 illustrates an example helical cone-beam CT dark field reconstruction method.

At 1502, a dark-field signal is obtained for a scanned object from a 360 degree scan.

At 1504, the dark field signal is weighted.

At 1506, the weighted dark-field signal is rebinned into wedge geometry.

At 1508, an aperture or angular weighted full scan back-projection reconstruction algorithm is applied to the weighted rebinned dark field signal over the 360 degree scan, as described herein.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
obtaining a dark-field signal generated from a dark-field CT scan of an object, wherein the dark-field CT scan is at least a 360 degree scan;
weighting the dark-field signal; and
performing a cone beam reconstruction of the weighted dark-field signal over the 360 degree scan, thereby generating volumetric image data.

2. The method of claim 1, wherein the cone beam reconstruction does not require a complementary dark-field signal for the scanned object, which is a signal acquired one hundred and eighty degrees apart from the dark-field signal.

3. The method of claim 1, wherein the cone beam reconstruction is an extension of a 2D filtered back-projection reconstruction over the 360 degree scan.

4. The method of claim 3, wherein the 2D filtered back-projection reconstruction includes a term that is a function of the complementary dark-field signal, and further comprising:
approximating the complementary dark-field signal in the term with the dark-field signal.

5. The method of claim 3, wherein the 2D filtered back-projection reconstruction includes applying a filtered back-projection to the weighted dark-field signal and multiplying a result of the filtered back-projection by a value of two.

6. The method of claim 1, wherein the dark-field CT scan is an axial cone-beam CT scan, and the cone-beam reconstruction is a 360 degree FDK cone beam reconstruction.

7. The method of claim 1, wherein the dark-field CT scan is a helical cone-beam CT scan.

8. The method of claim 7, further comprising:
rebinning the dark-field signal to a wedge geometry, and wherein the cone-beam reconstruction is an aperture weighted wedge reconstruction.

9. The method of claim 7, further comprising:
rebinning the dark-field signal to a wedge geometry, and wherein the cone-beam reconstruction is an angular weighted wedge reconstruction.

10. The method of any claim 9, wherein the weights of all views with distance $2\pi$ add to ½ independently.

11. An imaging system, comprising:
a source that emits radiation at a focal spot that traverses an examination region;
an interferometer that filters the emitted radiation for a dark-field imaging scan of an object; and
a detector array that detects the filtered radiation traversing the examination region and produces a dark-field signal indicative thereof; and
a reconstructor that weights the dark-field signal and reconstructs the weighted dark-field signal over 360 degrees using a cone beam reconstruction, generating volumetric image data,
wherein the cone beam reconstruction does not require a complementary dark-field signal for the scanned object, which is a signal acquired one hundred and eighty degrees apart from the dark-field signal.

12. The imaging system of claim 11, wherein the reconstructor applies a cone beam reconstruction that is an extension of a 2D filtered back-projection reconstruction over the 360 degrees.

13. The imaging system of claim 12, wherein the 2D filtered back-projection reconstruction includes a term that is a function of the complementary dark-field signal, which approximated with the dark-field signal.

14. The imaging system of claim 12, wherein the 2D filtered back-projection reconstruction includes applying a filtered back-projection to the dark-field signal and multiplying a result of the filtered back-projection by a value of two.

15. The imaging system of claim 11, wherein the dark-field CT scan is an axial cone-beam CT scan, and the reconstructor applies a 360 degree FDK cone beam reconstruction.

16. The imaging system of claim 11, wherein the dark-field CT scan is a helical cone-beam CT scan.

17. The imaging system of claim 16, wherein the reconstructor rebins the dark-field signal to a wedge geometry and applies an aperture weighted wedge reconstruction.

18. The imaging system of claim 16, wherein the reconstructor rebins the dark-field signal to a wedge geometry and applies an angular weighted wedge reconstruction.

19. A computer readable storage medium encoded with computer readable instructions, which, when executed by a processor, cause the processor to:
obtain a dark-field signal generated from at least a 360 degree dark-field CT scan of an object;
weight the dark-field signal; and
perform a cone beam reconstruction on the weighted dark-field signal over 360 degrees, thereby generating volumetric image data.

20. The computer readable storage medium of claim 19, wherein the dark-field CT scan is an axial cone-beam CT scan, and the cone-beam reconstruction is a full scan FDK cone beam reconstruction.

21. The computer readable storage medium of claim 20, wherein the dark-field CT scan is a helical cone-beam CT scan, and the computer readable instructions, which, when executed by the processer, further cause the processor to:
- rebin the dark-field signal to a wedge geometry; and
- apply at least one of a 360 degree aperture or angular weighted wedge reconstruction to the rebinned dark-field signal.

22. The computer readable storage medium of claim 19, wherein the cone-beam reconstruction is based on a fan-beam reconstruction.

23. The computer readable storage medium of claim 19, wherein the cone-beam reconstruction is based on a parallel-beam reconstruction.

* * * * *